United States Patent
Zhang et al.

(10) Patent No.: US 10,981,807 B1
(45) Date of Patent: Apr. 20, 2021

(54) DISINFECTING FLUID USING DISINFECTION LIGHT

(71) Applicant: Bolb Inc., Livermore, CA (US)

(72) Inventors: Jianping Zhang, Arcadia, CA (US); Huazhong Deng, Livermore, CA (US)

(73) Assignee: Bolb Inc., Livermore, CA (US)

( * ) Notice: Subject to any disclaimer, the term of this patent is extended or adjusted under 35 U.S.C. 154(b) by 0 days.

(21) Appl. No.: 16/595,490

(22) Filed: Oct. 8, 2019

(51) Int. Cl.
*C02F 1/32* (2006.01)
*A61L 2/10* (2006.01)

(52) U.S. Cl.
CPC .............. *C02F 1/325* (2013.01); *A61L 2/10* (2013.01); *A61L 2202/11* (2013.01); *C02F 2201/326* (2013.01); *C02F 2201/3222* (2013.01); *C02F 2201/3228* (2013.01); *C02F 2303/04* (2013.01)

(58) Field of Classification Search
CPC .............. C02F 1/325; C02F 2201/326; C02F 2201/3228; C02F 2201/3227; C02F 2303/04; C02F 2201/3222; C02F 2201/002; A61L 2/10; A61L 2202/11
See application file for complete search history.

(56) References Cited

U.S. PATENT DOCUMENTS

| | | | | |
|---|---|---|---|---|
| 4,011,456 A * | 3/1977 | Bredewater | ............ | B01J 19/123 250/492.1 |
| 5,600,744 A * | 2/1997 | Takahashi | ............ | G02B 6/4203 385/35 |
| 2002/0088945 A1 * | 7/2002 | Matschke | ................. | A61L 9/20 250/432 R |
| 2004/0061069 A1 * | 4/2004 | Schalble | ................... | A61L 2/10 250/432 R |
| 2005/0088655 A1 * | 4/2005 | Ellis | ........................ | G01J 1/429 356/436 |
| 2006/0169649 A1 * | 8/2006 | Hsueh | ................... | B08B 9/0321 210/764 |
| 2006/0231770 A1 * | 10/2006 | Snowball | ................ | C02F 1/325 250/432 R |
| 2008/0197291 A1 * | 8/2008 | Gerardi-Fraser | ......... | G01J 1/04 250/372 |
| 2010/0296971 A1 * | 11/2010 | Gaska | ....................... | A61L 2/10 422/62 |
| 2013/0119265 A1 * | 5/2013 | Anderle | ................ | A61L 2/0011 250/432 R |
| 2015/0144575 A1 * | 5/2015 | Hawkins, II | ............ | C02F 1/325 210/748.11 |
| 2017/0283276 A9 * | 10/2017 | Abe | ........................ | B01J 19/12 |
| 2017/0307234 A1 * | 10/2017 | Matschke | ................. | A61L 2/10 |
| 2018/0140729 A1 * | 5/2018 | Kiuchi | ................... | A61L 2/0047 |

(Continued)

*Primary Examiner* — Wyatt A Stoffa
(74) *Attorney, Agent, or Firm* — Patent Office of Dr. Chung Park

(57) ABSTRACT

Fluid disinfection apparatus for disinfecting liquid. The fluid disinfection apparatus includes: a first light source assembly for generating disinfection light that has a shape of a frustum; and a container for holding fluid therein. The container includes a first frustum shell defining a space surrounded by the top, base, and inner lateral surface thereof, wherein the inner lateral surface of the first frustum shell is substantially identical to a lateral surface of the frustum of the disinfection light and wherein the first light source assembly is disposed over the top of the first frustum shell so that the entire portion of the space is substantially located within the frustum of the disinfection light.

17 Claims, 15 Drawing Sheets

(56) References Cited

U.S. PATENT DOCUMENTS

| | | | |
|---|---|---|---|
| 2018/0208486 A1* | 7/2018 | Konagayoshi | A61L 2/10 |
| 2019/0135659 A1* | 5/2019 | Smetona | C02F 1/325 |
| 2019/0225509 A1* | 7/2019 | Dhiman | C02F 1/325 |
| 2019/0256379 A1* | 8/2019 | Kato | B01J 19/2415 |
| 2019/0263680 A1* | 8/2019 | Dobrinsky | C02F 1/325 |

* cited by examiner

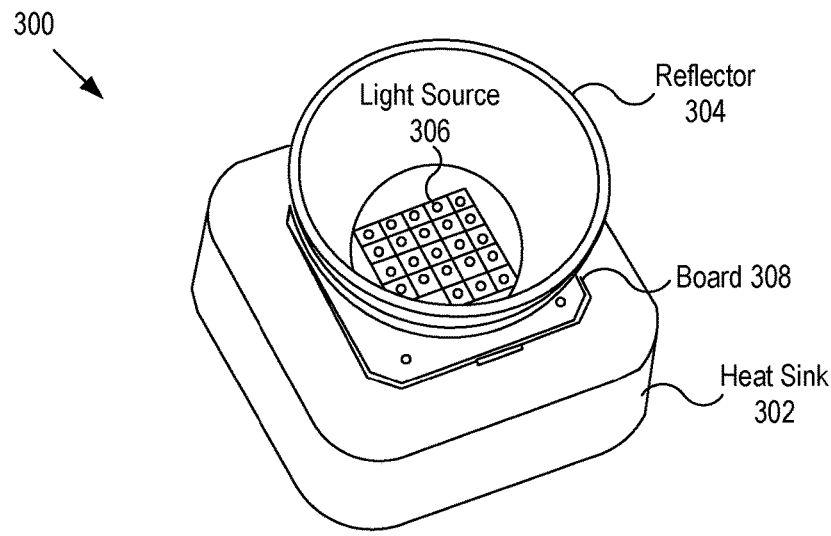
FIG. 3A
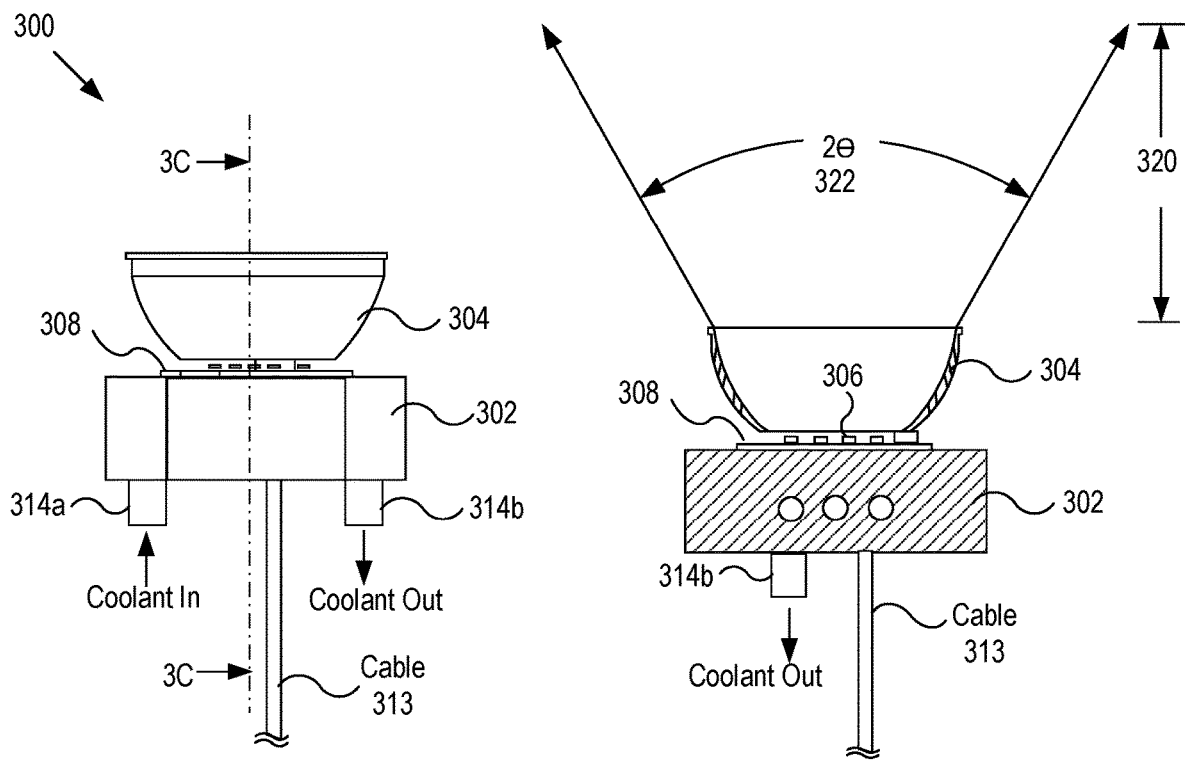
FIG. 3B
FIG. 3C

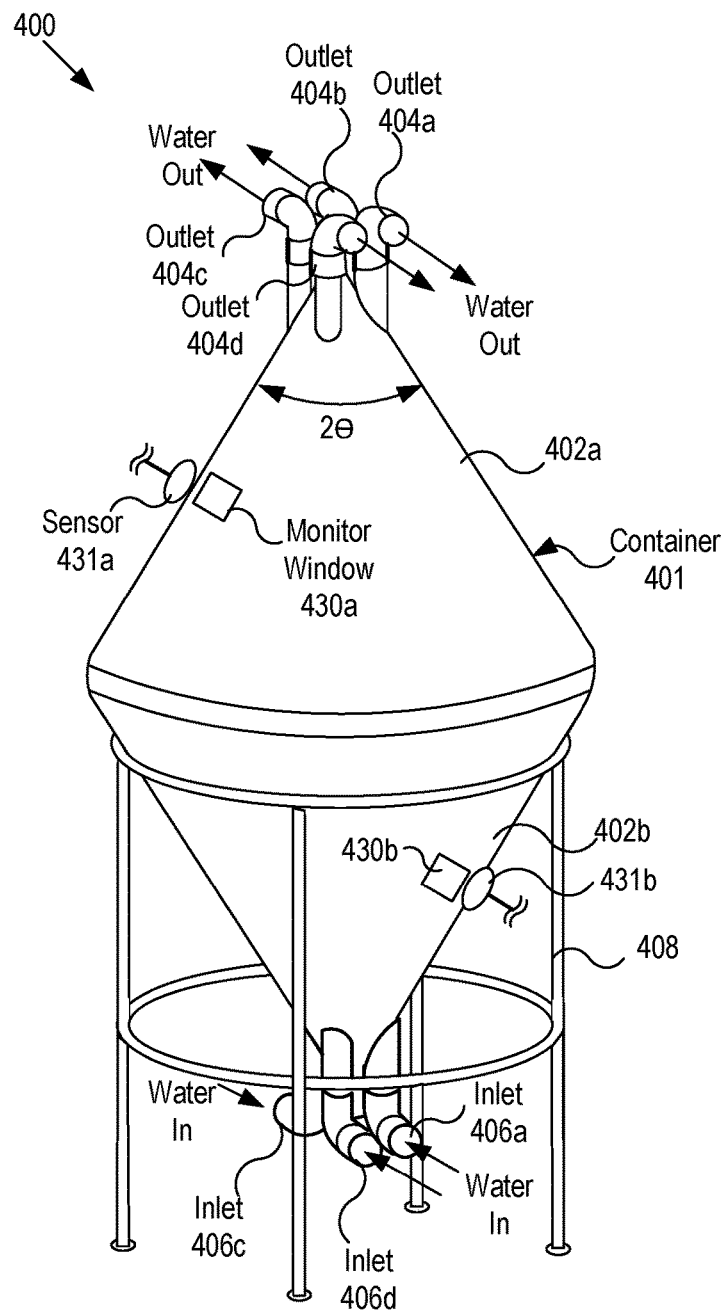
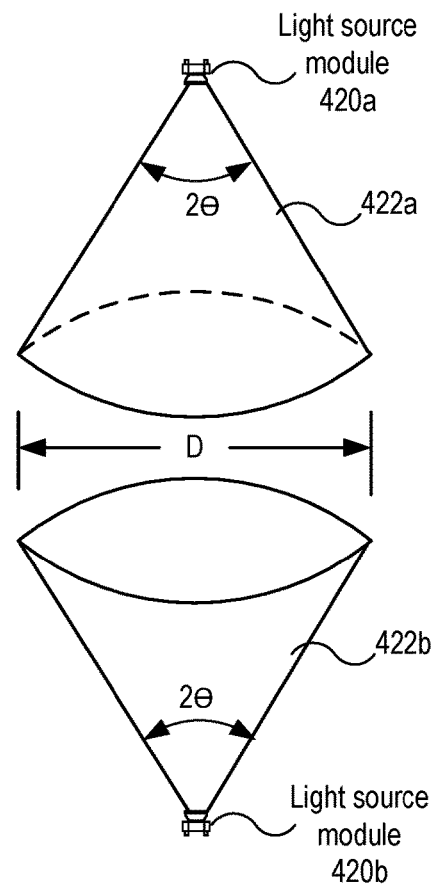
FIG. 4
FIG. 6

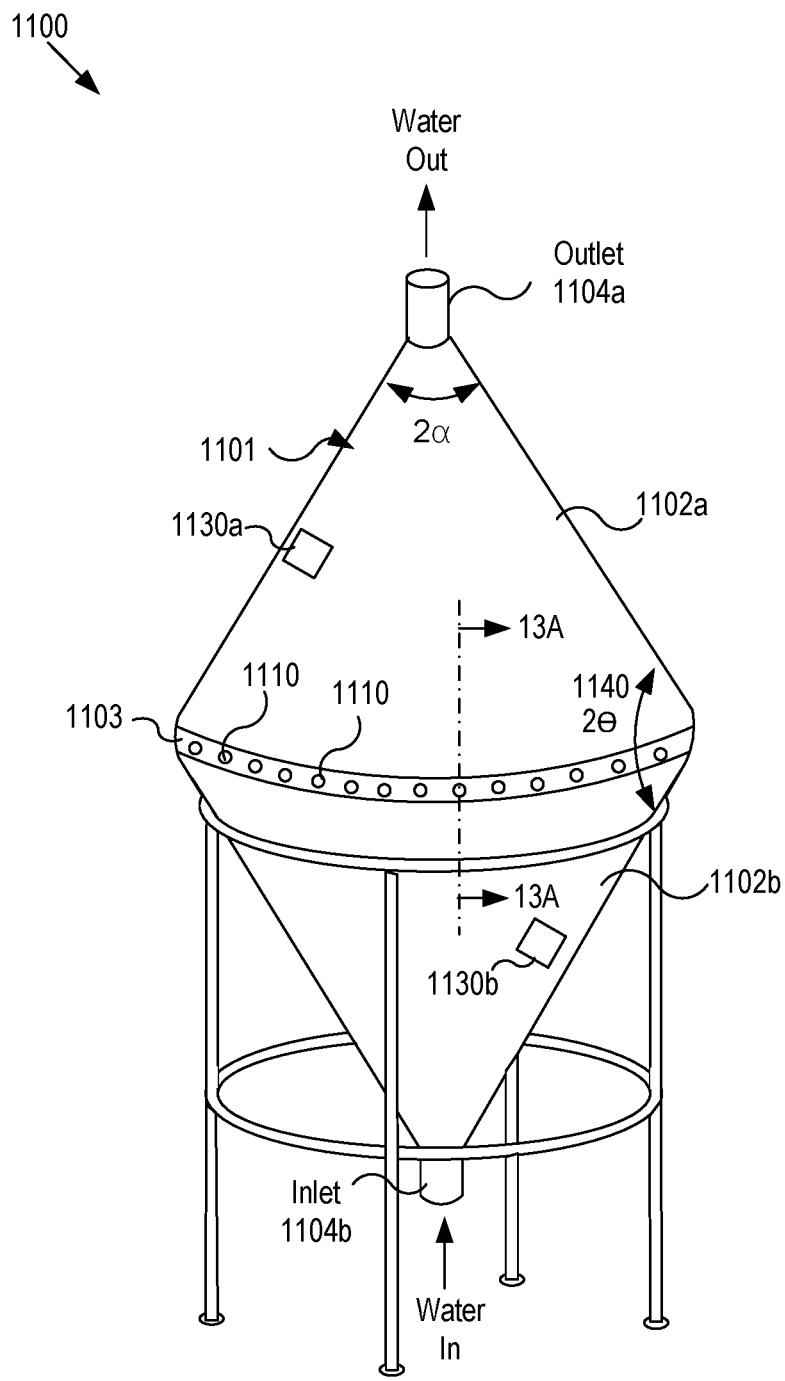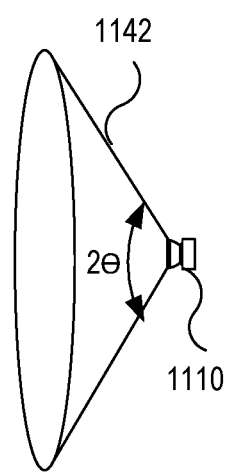
FIG. 11
FIG. 12

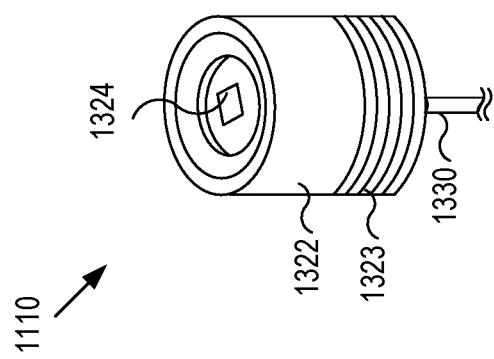
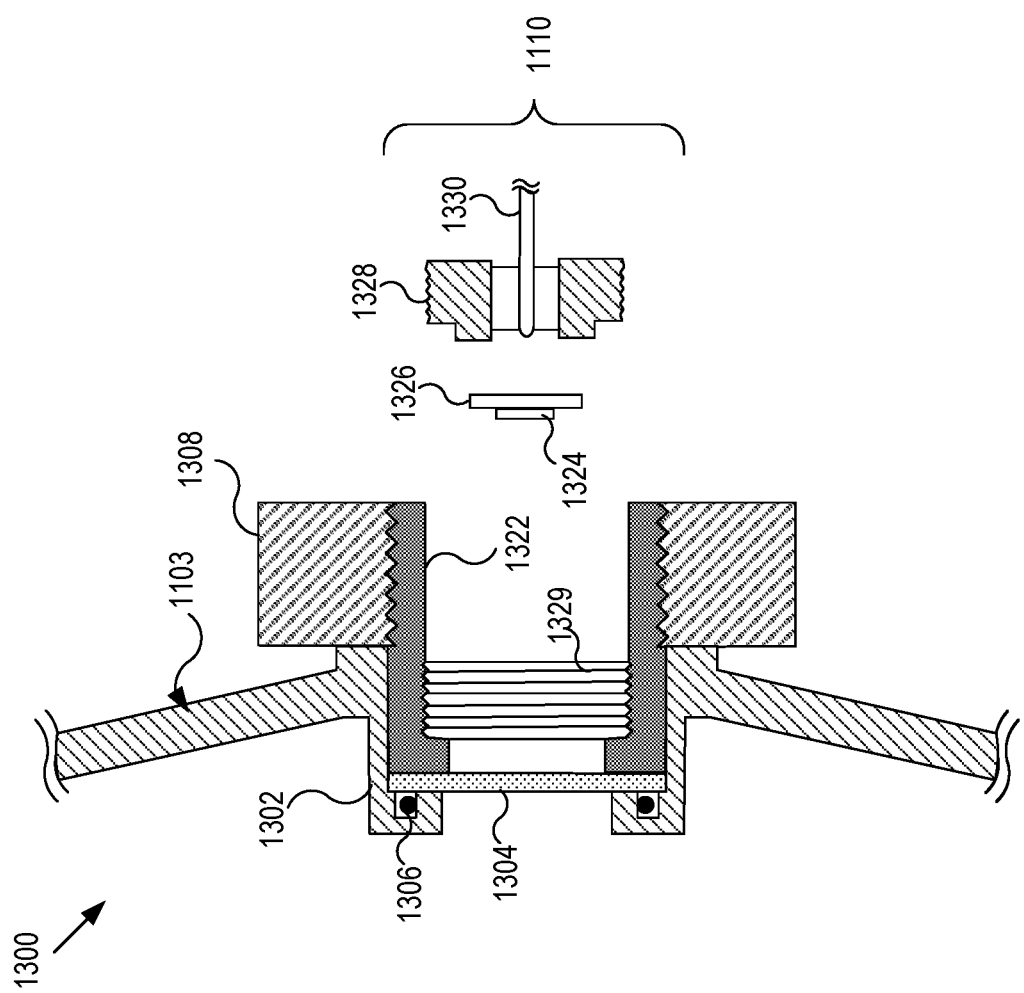
FIG. 13B
FIG. 13A

DISINFECTING FLUID USING DISINFECTION LIGHT

BACKGROUND

A. Technical Field

The present invention relates to devices for disinfecting fluid, and more particularly, to fluid disinfection apparatus using disinfection light.

B. Background of the Invention

Water and other liquids may carry infectious pathogenic microorganisms, such as bacteria, spores, viruses, and fungi, that need to be disinfected/sterilized to protect public health. UV light is known to have germicidal properties and has been developed as the disinfection light source. Specifically, the mechanism by which UV light kills microorganisms is by damaging the genetic material, the deoxyribonucleic acid (DNA), of the microorganisms and wavelengths between 200-300 nm have been shown to initiate a photoreaction between adjacent pyrimidines.

In general, different microbes have different UV disinfection dosages. When using the conventional low-pressure mercury lamp UV emissions at 254 nm, the National Sanitation Foundation (NSF) Standard 55-1991 Ultraviolet Microbiological Water Treatment Systems demand the NSF failsafe set-point dosage for Class A systems UV water treatment system is 40 mJ/cm$^2$, and International Water-Guard designs its Class A units to operate at a minimum dosage of 40 mJ/cm$^2$ as well. Class A systems are those designed to disinfect water contaminated by micro-organisms like bacteria and viruses, but not water with an obvious contamination source such as raw sewage, nor are they designed to convert wastewater to safe drinking water. Class B systems are intended to provide supplemental treatment of drinking water that has been tested by health authorities and deemed acceptable for human consumption. The NSF dosage requirement for Class B systems using 254 nm emission is 16 mJ/cm$^2$. Use of 265-275 nm UV emissions for disinfection, which have the maximal UV germicidal effect, can reduce the required dosage for the same germicidal effect as compared to the use of 254 nm UV light. UV emissions at 265 nm and in the range of 200 nm to 400 nm can be generated by group III nitride semiconductor UV light emitting diodes (LEDs).

To effectively deliver failsafe set-point dosages to fluid in motion, the flow passageway and/or chamber need to be designed to avoid UV power loss on the inner walls thereof. FIG. 1 shows a UV disinfection system 100 for disinfecting fluid in a pipe 102, where the direction of the UV light is parallel to the fluid flow. According to the Lambert's law, the UV dosage, J, which represents a UV power delivered to a unit area of the pipe as the fluid travels the distance L, may be expressed as Equation (1):

$$J = \int_0^L \frac{P}{S} e^{-\alpha x} \frac{dx}{v} = \frac{P}{S\alpha v}(1 - e^{-\alpha L}) = \frac{P}{\alpha G}(1 - e^{-\alpha L}) \quad (1)$$

where P, S, $\alpha$, v, and G (=Sv) represent the total UV power incident on the pipe 102, cross sectional area of the pipe 102, absorption coefficient of the fluid, fluid velocity, and the flow rate in the pipe, respectively. As shown in Equation (1), the power dosage, J, is a function of the flow rate G, absorption coefficient $\alpha$, and the distance L. FIG. 2 shows a plot of UV dosage, J, as a function of the absorption coefficient under an exemplary condition: P=4000 mW, G=100 Gallons/min, and L=150 cm.

It is noted that the UV dosage, J, in Equation (1) is not a function of the cross section, S, i.e., the UV dosage is not a function of the geometrical shape of the pipe. It is because the Equation (1) is derived under the assumption that the UV light travels parallel to the flow direction. However, in general, UV light source, such as ultraviolet light emitting diode (UV LED), is a point light source and the light from the UV source is not a collimated beam. As such, an optical arrangement is required to collimate the light from the point light source. Typically, the components of the optical arrangement for collimating the UV light may absorb the UV light, to thereby decrease the efficiency of the UV disinfection system.

It is also noted that the UV dosage, J, in Equation (1) increases as the length L increases, and as such, an engineer may need to design the flow system such that the path length of the light is maximized and/or the path length of the light is longer than a minimum path length, $L_{min}$, for delivery of a required failsafe UV dosage. However, if light is not parallel to the pipe 102, light may reflect a few times on the inner wall of the pipe 102 and get absorbed before traveling the distance $L_{min}$. To decrease the loss of light on the inner wall due to the reflection, the inner wall of the pipe 102 may be coated with a reflecting material. Since a typical reflective coating material, such as aluminum, has a reflectance of 90%, the intensity of the light may decrease by 27% upon reflecting three times on the aluminum coated pipe wall, for instance. Furthermore, coating the pipe wall increases the total manufacturing cost of the disinfection system. Thus, there is a need for a flow chamber design that can efficiently deliver the failsafe UV dosage to the fluid without reflecting the UV light generated by a conventional UV light source.

SUMMARY OF THE DISCLOSURE

In one aspect of the present invention, a disinfection method using UV disinfection light to disinfect a fluid comprises steps: engineering divergence of the disinfection light and determining a disinfection light cone, pyramid, or frustum; designing a fluid container to define a volume of disinfection, wherein the volume of disinfection substantially coincides with the disinfection light cone, pyramid, or frustum.

In another aspect of the present invention, a fluid disinfection apparatus includes: a first light source assembly for generating disinfection light that has a shape of a frustum; and a container for holding fluid therein. The container includes a first frustum shell defining a space surrounded by the top, base, and inner lateral surface thereof, where the inner lateral surface of the first frustum shell is substantially identical to the lateral surface of the frustum of the disinfection light and where the first light source assembly is disposed over the top of the first frustum shell so that the entire portion of the space is substantially located within the frustum of the disinfection light.

In another aspect of the present invention, a fluid disinfection apparatus includes: at least one light source assembly for generating disinfection light that has a shape of a conical frustum; and a container for holding fluid therein. The container includes: a first conical frustum shell; and a second conical frustum shell, where the base of the first conical frustum shell is joined to the base of the second conical frustum shell to form a circular ring, and where the at least one light source assembly is disposed on the circular ring. The aperture angle of the conical frustum of the disinfection light is substantially same as an angle between the first and second conical frustum shells at the circular ring.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIG. 3A shows a perspective view of a light source module according to embodiments of the present disclosure.

FIG. 3B shows a side view of the light source module in FIG. 3A according to embodiments of the present disclosure.

FIG. 3C shows a cross sectional view of the light source module in FIG. 3B, taken along the line 3C-3C according to embodiments of the present disclosure.

FIG. 4 shows a perspective view of a fluid disinfection apparatus according to embodiments of the present disclosure.

FIG. 6 shows light cones from the light source modules in FIG. 4 according to embodiments of the present disclosure.

FIG. 11 shows a perspective view of a fluid disinfection apparatus according to embodiments of the present disclosure.

FIG. 12 shows a light cone from a light source module in FIG. 11 according to embodiments of the present disclosure.

FIG. 13A shows an exploded cross-sectional view of the light source assembly in FIG. 11, taken along the line 13A-13A according to embodiments of the present disclosure.

FIG. 13B shows a perspective view of the light source module in FIG. 13A according to embodiments of the present disclosure.

DETAILED DESCRIPTION OF THE PREFERRED EMBODIMENTS

Figure 1:
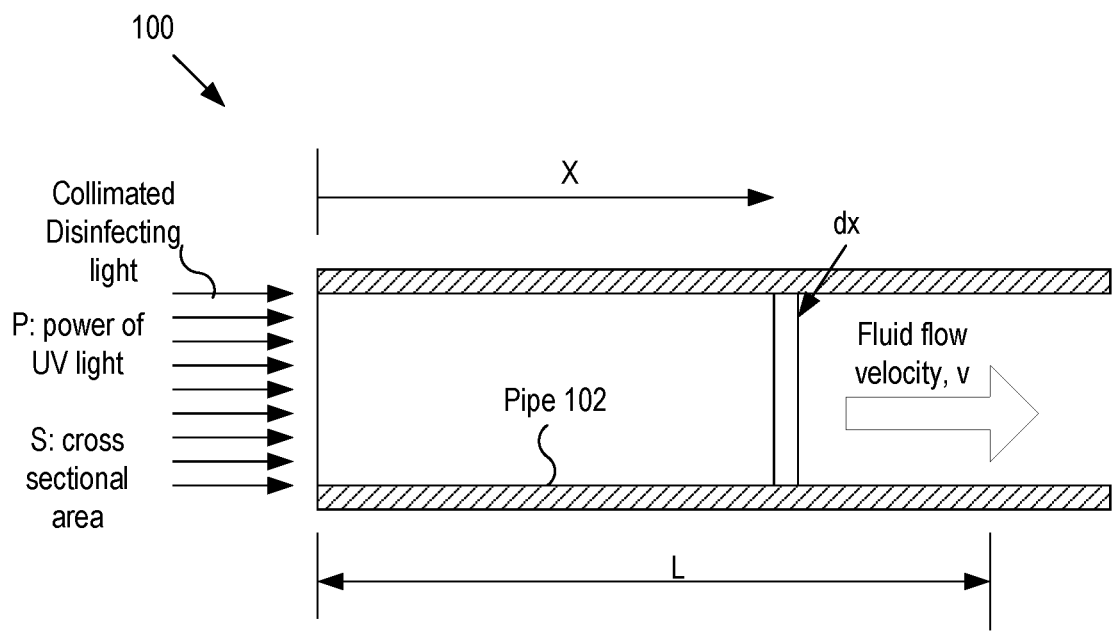
FIG. 1 shows a UV disinfection system for disinfecting fluid in a pipe.
Figure 2:
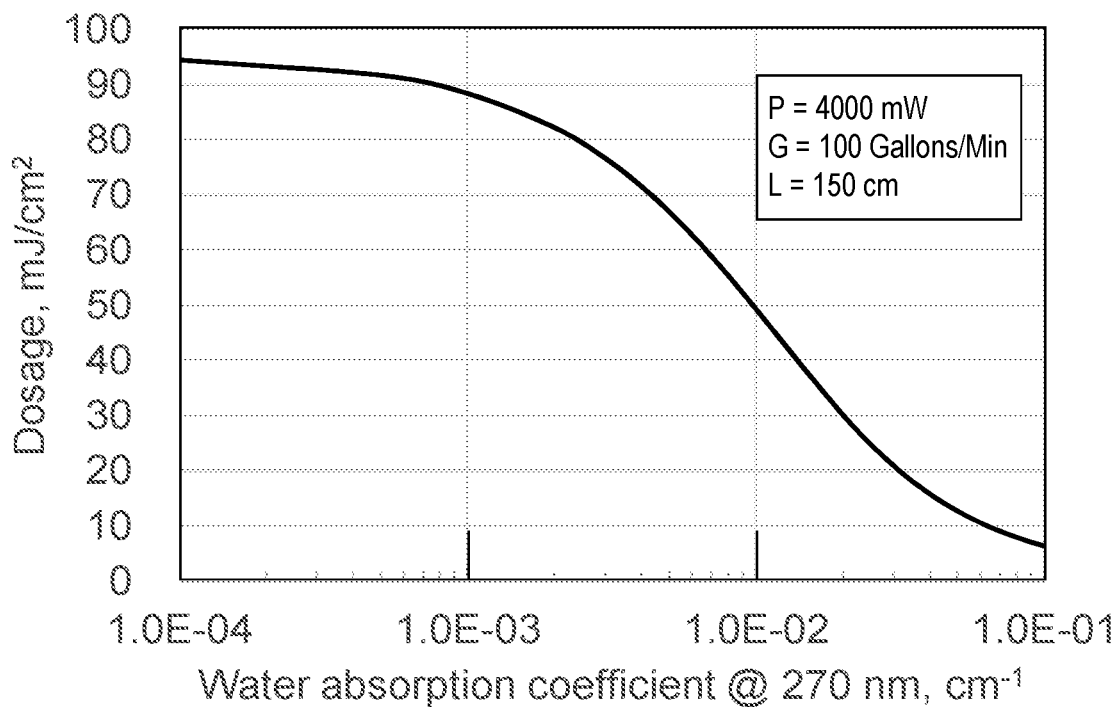
FIG. 2 shows a plot of UV dosage as a function of an absorption coefficient.

In the following description, for the purposes of explanation, specific details are set forth in order to provide an understanding of the disclosure. It will be apparent, however, to one skilled in the art that the disclosure can be practiced without these details. One skilled in the art will recognize that embodiments of the present disclosure, described below, may be performed in a variety of ways and using a variety of means. Those skilled in the art will also recognize additional modifications, applications, and embodiments are within the scope thereof, as are additional fields in which the disclosure may provide utility. Accordingly, the embodiments described below are illustrative of specific embodiments of the disclosure and are meant to avoid obscuring the disclosure.

A reference in the specification to "one embodiment" or "an embodiment" means that a particular feature, structure, characteristic, or function described in connection with the embodiment is included in at least one embodiment of the disclosure. The appearance of the phrase "in one embodiment," "in an embodiment," or the like in various places in the specification are not necessarily all referring to the same embodiment.

FIG. 3A shows a perspective view of a light source module 300 according to embodiments of the present disclosure. FIG. 3B shows a side view of the light source module 300 according to embodiments of the present disclosure. FIG. 3C shows a cross sectional view of the light source module 300, taken along the line 3C-3C according to embodiments of the present disclosure. As depicted, the light source module 300 may include: a heat sink 302; a board 308 mounted on the heat sink; a light source 306 for generating a disinfection light, such as UV light, and mounted on and controlled by the board 308; a reflector 304 that guides the direction of the light from the light source 306 (i.e., guiding the light into a shape of a conical frustum 320); an inlet 314a and an outlet 314b through which the coolant for cooling the heat sink flows; and a cable 313 for providing control signals and electrical power to the board 308. In the following sections, the light source 306 is assumed to generate UV light, even though the light source can generate disinfection lights having other suitable wavelengths. In embodiments, the light source 306 may be UV LEDs or UV LED arrays forming a germicidal light panel.

In embodiments, the board 308, which may be a printed circuit board (PCB), made mainly of aluminum or copper, may include electrical circuits for controlling the electrical power to the light source 306. In embodiments, the light source 306 may include one or more ultraviolet light emitting diodes (UV LEDs). During operation, the heat energy generated by the PCB board and the light source 306 may be transferred to the heat sink 302, and the coolant flowing through the heat sink may take the heat energy from the heat sink.

In embodiments, the reflector 304 may have a shape of a curved-cone (or bell) or a paraboloid so that light leaving the reflector 304 may have a shape of a right circular frustum with an aperture angle (or cone angle) 322, 2θ. Hereinafter, the aperture angle of a right circular conical frustum (or a circular cone) refers to the maximum angle between any two generatrix lines of the right circular conical frustum (or a circular cone). It is noted that the light source module 300 may have other elements and design so that the conical frustum of light 320 generated by the light source module 300 has the aperture angle 322, 2θ.

Figure 5:
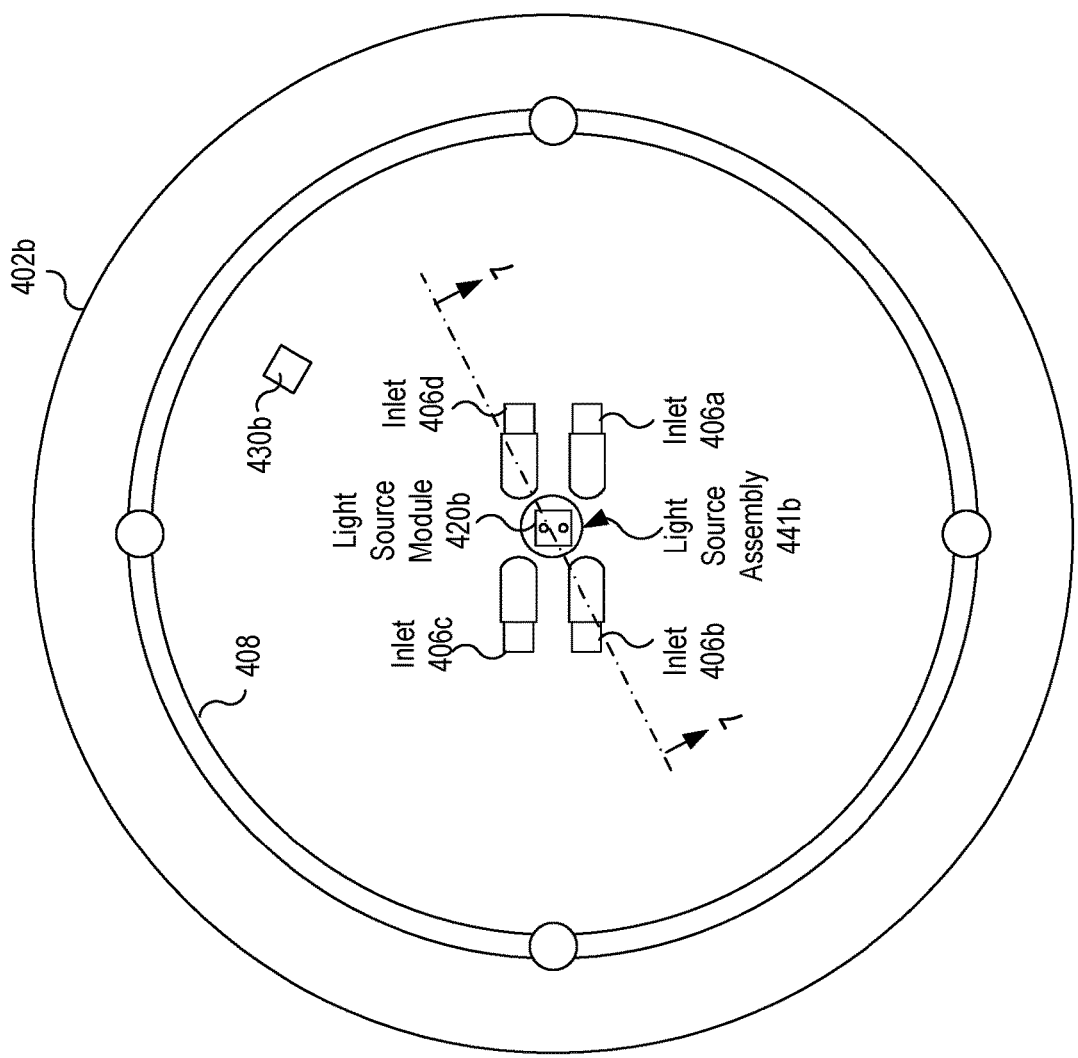
FIG. 5 shows a bottom view of the fluid disinfection apparatus in FIG. 4 according to embodiments of the present disclosure.

FIG. 4 shows a perspective view of a fluid disinfection apparatus 400 according to embodiments of the present disclosure. FIG. 5 shows a bottom view of the fluid disinfection apparatus 400 according to embodiments of the present disclosure.

As depicted, the fluid disinfection apparatus 400 may include: a tank (container) 401 having two conical frustum shells 402a and 402b; one or more inlets 406a-406d and one or more outlets 404a-404d, where the fluid to be disinfected may flow into the container 401 through the inlets and the disinfected fluid may flow out of the container through the outlets; and one or more disinfection light assemblies (including 441b) disposed between the one or more inlets 406a-406d and/or the one or more outlets 404a-404d and configured to generate the disinfection light for disinfecting the fluid. In embodiments, the container 401 may be mounted on a stand 408. For the purpose of illustration, the fluid is assumed to be water, even though the fluid disinfection apparatus 400 may be used to disinfect various types of fluid.

FIG. 6 shows two frusta of light 422a and 422b from light source modules 420a and 420b, respectively, according to embodiments of the present disclosure. In embodiments, the light source modules 420a and 420b may be similar to the light source module 300 in FIG. 3A. As depicted, each light frustum (e.g. 422a) may have an aperture angle, 2θ, where the corresponding conical frustum shell 402a may have substantially the same aperture angle so that the light in the light frustum is absorbed by the fluid without being reflected on the inner lateral surface of the conical frustum shell 402a. In embodiments, the base diameter D of the light frusta 422a may be substantially the same as the inner base diameter of the conical frustum shell 402a, and, as such, the light in the light frustum 422a has the minimum path length of $D/(2\sin(\theta))$, where the minimum path length refers to the distance that the light travels without being incident on the inner surface of the container 401.

If the aperture angle of the conical frustum shell 402a is smaller than the aperture angle of the light frustum 422a, some portion of the light in the light frustum 422a may be reflected on the inner wall of the conical frustum shell 402a, decreasing the minimum path length. If the aperture angle of the conical frustum shell 402a is larger than the aperture angle of the light frustum 422a, the fluid located outside the light frustum 422a may not be properly disinfected, i.e., the disinfection efficiency may decrease. Thus, by making the aperture angle of the conical frustum shell 402a be substantially the same as the aperture angle of the light frustum 422a, the minimum path length of the light in the light frustum 422a may be maximized to thereby increase the disinfection efficiency. In embodiments, the disinfection light frustum 422a (or 422b) may substantially identical to the volume (or space) defined by the top, base, and the inner lateral (or side) surface of the conical frustum shell 402a (or 402b) of the container. Hereinafter, the term volume of disinfection may refer to the volume (or space) surrounded by the top, base and the inner lateral surface of the frustum shell (e.g. 402a). In embodiments, the lateral (or side) surface of the light frustum 422a (or 422b) may be substantially identical to the inner lateral (or side) surface of the conical frustum shell 402a (or 402b) so that the entire portion of the volume of disinfection is located within the light frustum 422a while the light frustum 422a (or 422b) is not touching the inner lateral (or side) surface of the conical frustum shell 402a (or 402b). In embodiments, unlike the conventional system in FIG. 1, the light from the light source module 420a does not need to be collimated or steered to avoid the reflection on the inner wall of the conical frustum shell 402a, i.e., the minimum path length is maximized without using any optical arrangement or coating material.

In embodiments, one or more monitor windows 430a and 430b may be disposed on the container wall, where the windows may be formed of a material that is transparent to the disinfection light. In embodiments, UV sensors 431a and 431b may detect the intensity of the disinfection light through the monitor windows 430a and 430b, respectively.

In embodiments, the light intensity measured by the UV sensors 431a and 431b may be used to control the electrical power to the light sources of the light source modules 420a and 420b, forming a feedback loop for controlling the light source modules. For instance, the light sources may be UV light emitting diodes (LEDs) and their output intensity may slowly decrease over time in a process, known as lumen depreciation. In another example, the intensity of light from the light sources may need to be adjusted in response to the variation of the flow rate through the inlets 406a-406d. In embodiments, the feedback loop including the light sensors 431a and 431b may be used to control the power to the light sources, to thereby maintain a targeted UV intensity level and/or deliver a required UV dosage to the fluid in the container 401.

In general, light passing through water may be refracted by air bubbles in the water, reducing the minimum path length. In embodiments, the inlets 406a-406d may be disposed on the bottom side of the container 401 so as to reduce formation of air bubbles in the water during the process of filling the water into the container. It is noted that the number of inlets and/or outlets may be changed to meet the flow rate into the container 401.

Figure 7:
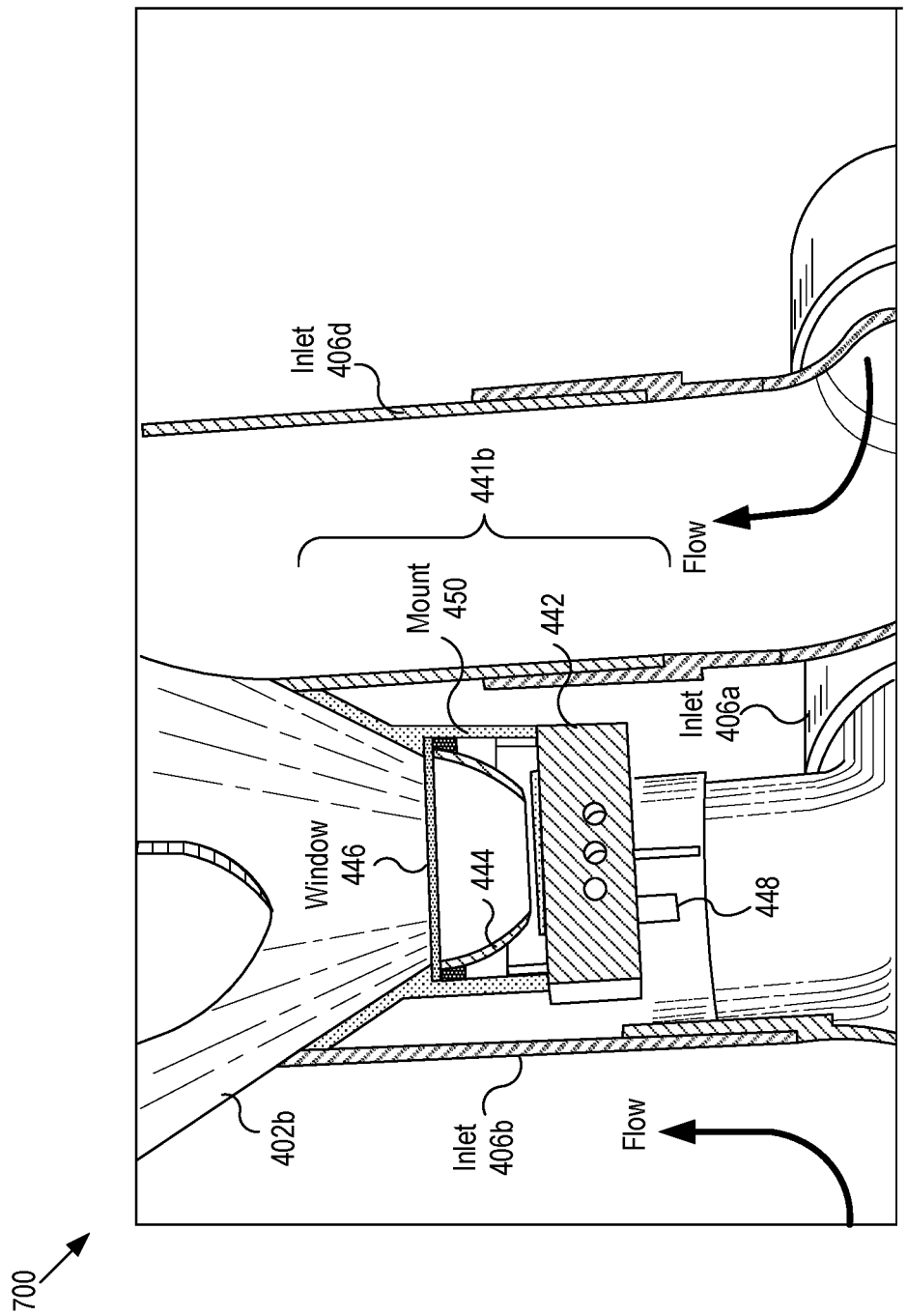
FIG. 7 shows a cross sectional view of the fluid disinfection apparatus in FIG. 5, taken along the line 7-7 according to embodiments of the present disclosure.
Figure 8:
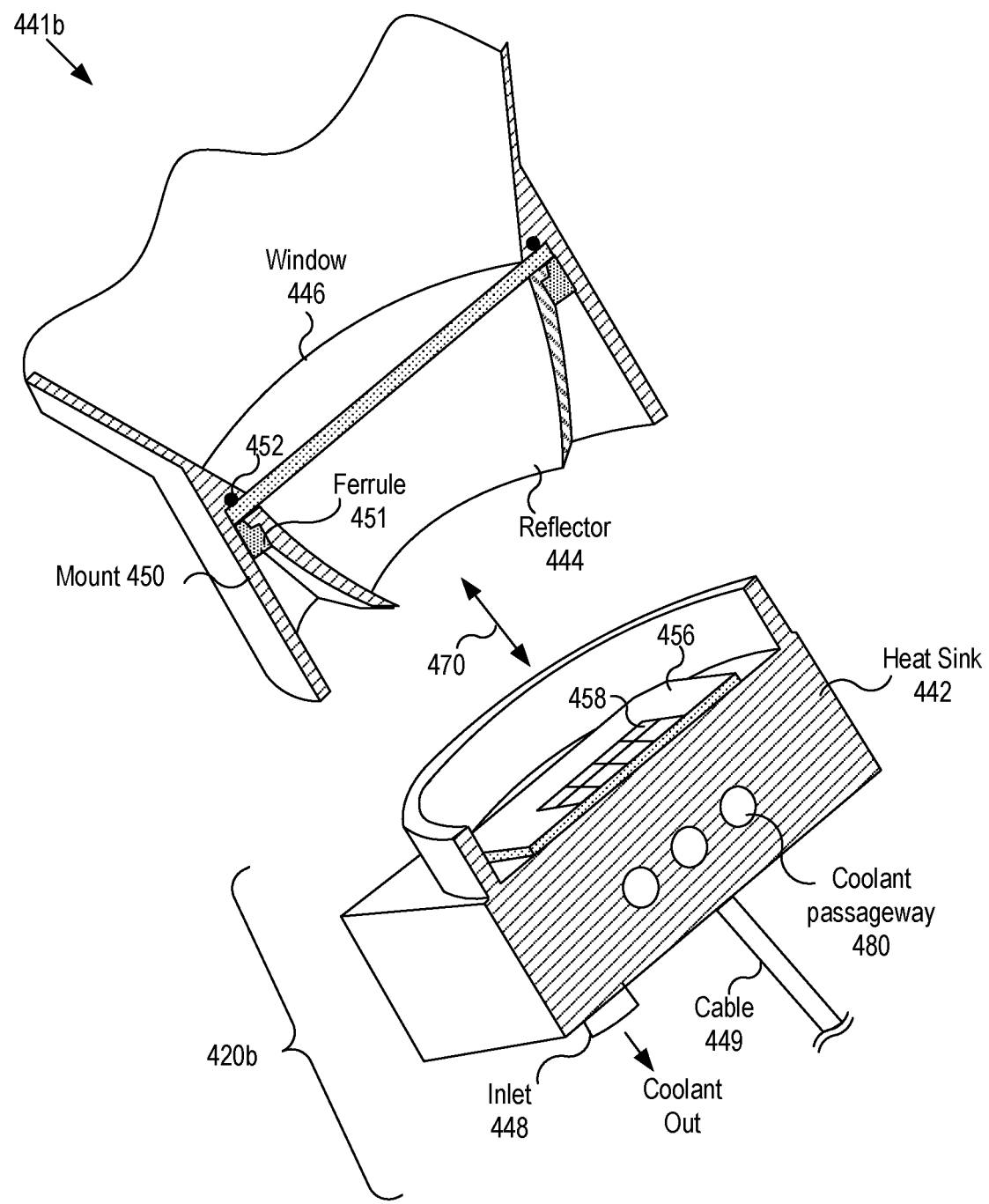
FIG. 8 shows an exploded cross-sectional view of the light source assembly in FIG. 7 according to embodiments of the present disclosure.

FIG. 7 shows a cross sectional view 700 of a portion of the fluid disinfection apparatus 400, taken along the line 7-7 in FIG. 5 according to embodiments of the present disclosure. FIG. 8 shows an exploded cross sectional view of the light source assembly 441b according to embodiments of the present disclosure. In embodiments, another light source assembly (not shown in FIG. 4) that is similar to the light source assembly 441b may be installed on the top portion of the conical frustum shell 402a and disposed between the outlets 404*a*-404*d*. In embodiments, as discussed above, each light source assembly may be installed on the top portion of the corresponding conical frustum shell so that the light in the light cone from each light source assembly may travel toward the base of the corresponding conical frustum shell.

As depicted, the light source assembly 441*b* may include: a mount 450 for mounting a light source module thereto; a window 446; and a light source module 420*b* detachably mounted to the mount 450 along a direction 470. In embodiments, the light source assembly 441*b* may further include: a ferrule 451 for pushing the window 446 against the mount 450 so that the O-ring 452 is compressed to provide a sealing between the window 446 and the mount 450. The ferrule 451 may also detachably secure the reflector 444 to the mount 450. In embodiments, the window 446 may be formed of a material that is transparent to the light generated by the light source 458. The material of choice may include sapphire, quartz, et al.

In embodiments, the light source module 420*b* may include: a heat sink 442 having a coolant passageway 480 formed therein; a board 456 mounted on the heat sink 442; a light source 458 mounted on and controlled by the board 456 and generating the disinfection light; an inlet 448 for introducing the coolant into the heat sink; an outlet (not shown in FIG. 8) for discharging the coolant from the heat sink; and a cable 449 for providing electrical power and signal to the board 456. The components of the light source module 420*b* may be similar to their counterparts of the light source module 300.

In one exemplary application of the fluid disinfection apparatus 400, the two conical frustum shells 402*a* and 402*b* are identical, each having an aperture angle of 2θ=60° and a top and a base diameter of 9.8 and 183 cm, respectively. The two light source modules 420*a* and 420*b* are identical and installed on the respective top portions of the two conical frustum shells 402*a* and 402*b*, each generating a UV light frustum of optical power 25 W and aperture angle of 60°. This apparatus is capable of disinfecting clear flowing water of 300 gallons/minute with UV dosage of 20 mJ/cm$^2$.

In another exemplary application of the fluid disinfection apparatus 400, the two conical frustum shells 402*a* and 402*b* are identical, each having an aperture angle of 2θ=60° and a top and a base diameter of 200 and 662 cm, respectively. The two identical light source modules 420*a* and 420*b* are identical and installed on the respective top portions of the two conical frustum shells 402*a* and 402*b*, each generating a UV light frustum of optical power 750 W and aperture angle of 60°. This apparatus is capable of disinfecting clear flowing water of 89,871 gallons/minute with UV dosage of more than 40 mJ/cm$^2$.

Figures 9A, 9B:
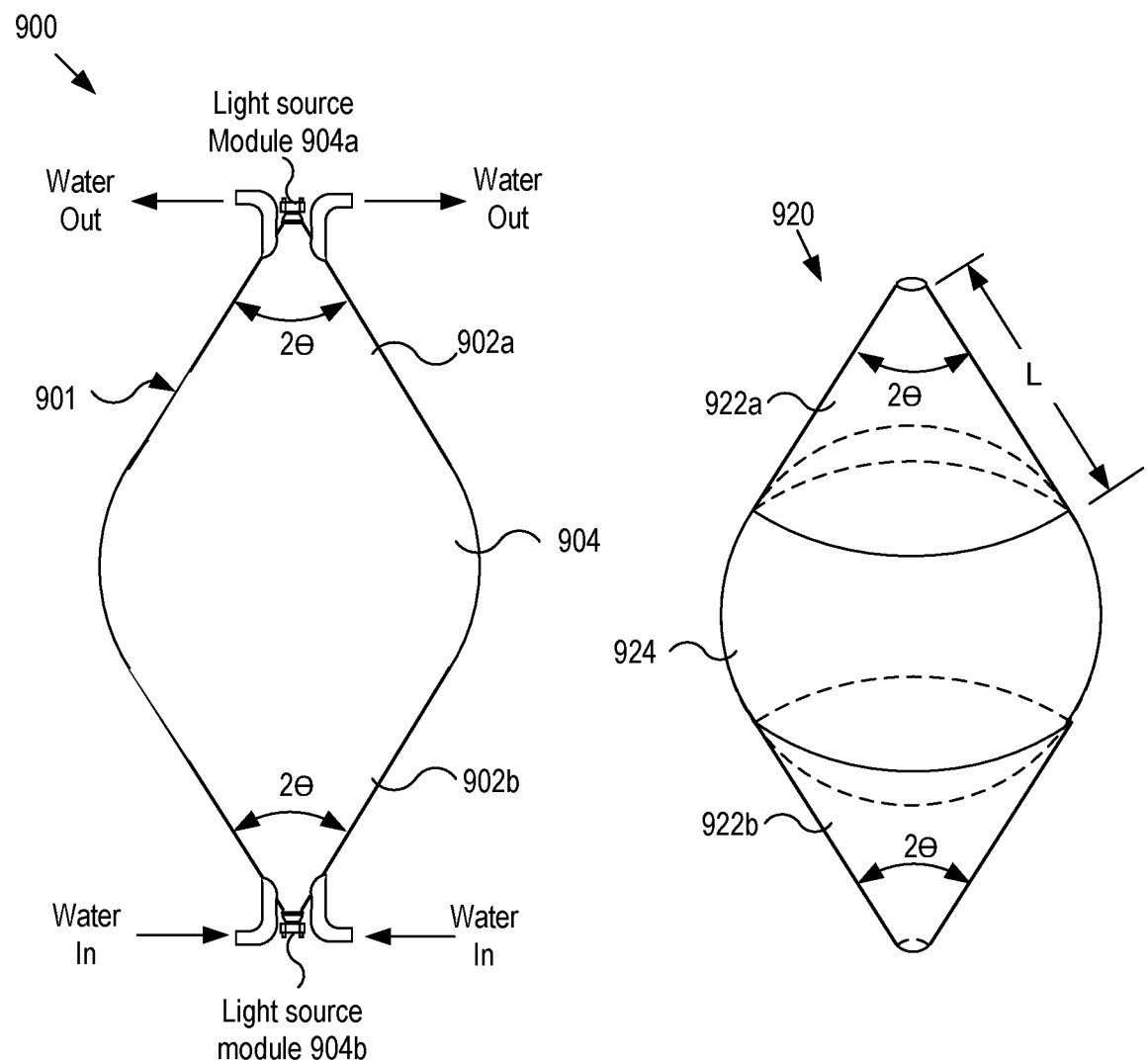
FIG. 9A shows a side view of a fluid disinfection apparatus according to embodiments of the present disclosure.
FIG. 9B shows a geometrical representation of the container in FIG. 9A according to embodiments of the present disclosure.

FIG. 9A shows a side view of a fluid disinfection apparatus 900 according to embodiments of the present disclosure. FIG. 9B shows a geometrical representation 920 of a container 901 according to embodiments of the present disclosure. As depicted, the fluid disinfection apparatus 900 may be similar to the fluid disinfection apparatus 400 in FIG. 4, with the difference that the container 901 includes: two conical frustum shells 902*a* and 902*b*; and a portion of a spherical shell 904 that is tangentially joined to the two conical frustum shells. (In the fluid disinfection apparatus 400, the base of the conical frustum shell 402*a* is directly joined to the base of the conical frustum shell 402*b*.) In FIG. 9B, the two conical frusta 922*a* and 922*b* correspond to the conical frustum shells 902*a* and 902*b*, respectively, and the sphere 924 corresponds to the spherical shell 904. In embodiments, the bases of the two cones 922*a* and 922*b* may be tangent to the sphere 924. As such, compared to the container 401, the minimum path length L of the light generated by a light source module 904*a* (or 904*b*) may not be changed while the total volume of the container 901 is increased due to the spherical portion 904.

In embodiments, each of the light source modules 904*a* and 904*b* may be similar to the light source module 420*b* and mounted to a light source assembly (not shown in FIG. 9A) in the same manner as the light source module 420*b* is mounted to the mount 450 of the light source assembly 441*b*.

Figure 10B:
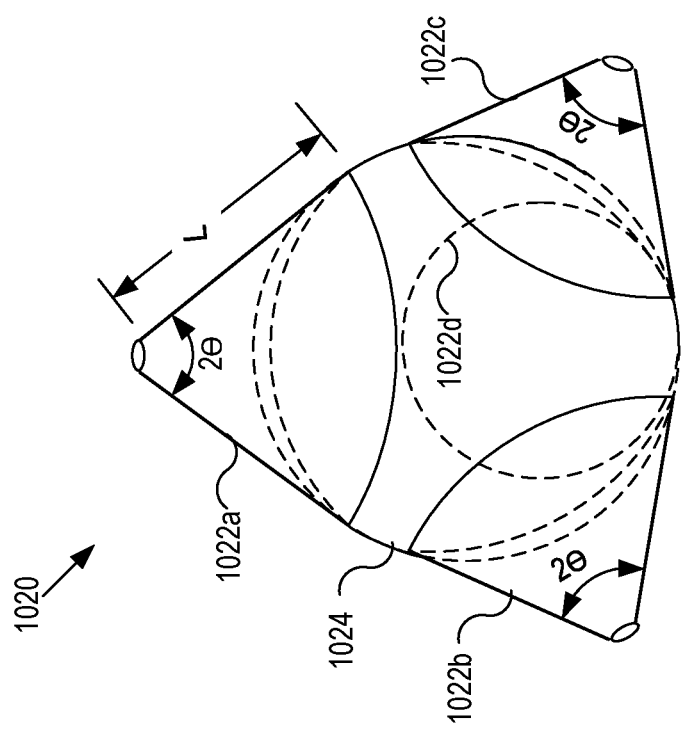
FIG. 10B shows a geometrical representation of the container in FIG. 10A according to embodiments of the present disclosure.
Figure 10A:
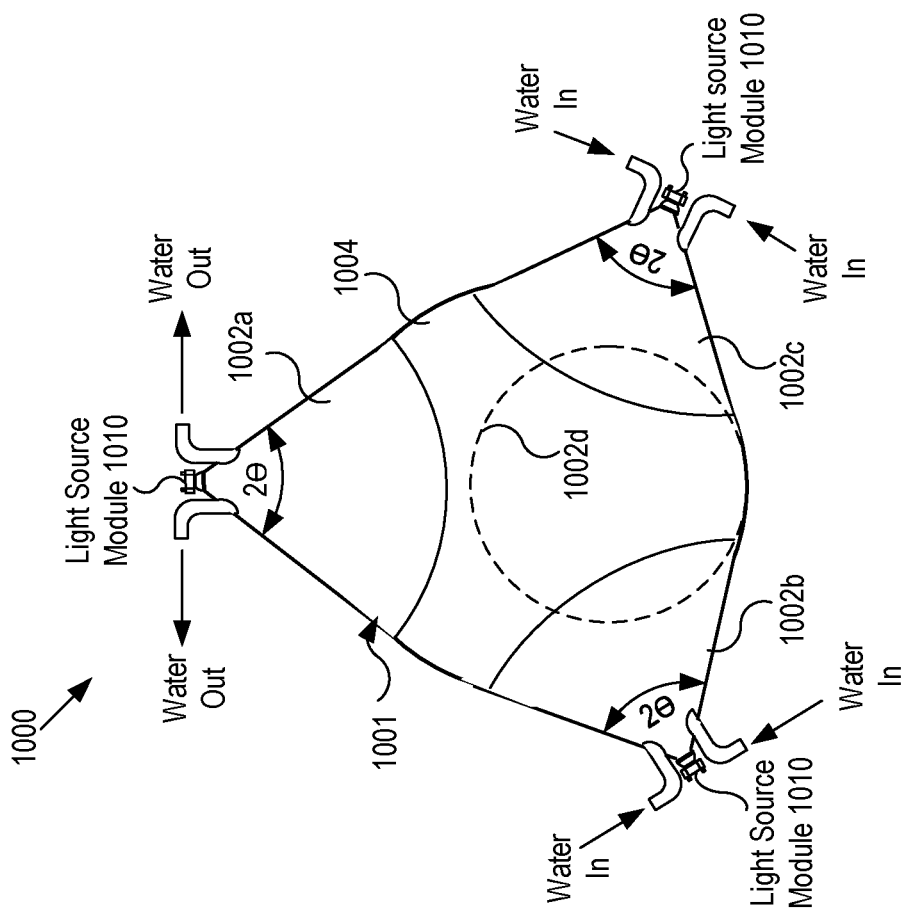
FIG. 10A shows a side view of a fluid disinfection apparatus according to embodiments of the present disclosure.

FIG. 10A shows a side view of a fluid disinfection apparatus 1000 according to embodiments of the present disclosure. FIG. 10B shows a geometrical representation 1020 of the container 1001 in FIG. 10A according to embodiments of the present disclosure. As depicted, the fluid disinfection apparatus 1000 may be similar to the fluid disinfection apparatus 900, with the difference that the fluid disinfection apparatus 1000 contains four conical frustum shells 1002*a*-1002*d*, where each of the three bottom side conical frustum shells 1002*b*-1002*d* may have a light source assembly and one or more inlets. The conical frustum shell 1002*a* may have a light source assembly and one or more outlets. It is noted that each of the inlets may be used as an outlet, or vice versa. For instance, one or more of the inlets of the conical frustum shell 1002*b* may be used as an outlet. In embodiments, each of the light source assembly in FIG. 10A may be similar to the light source assembly in 441*b* in FIG. 8.

As depicted in FIG. 10B, the four conical frusta 1022*a*-1022*d* may correspond to the four conical frustum shells 1002*a*-1002*d*, and the sphere 1024 may correspond to the spherical shell 1004. As depicted, the four conical frustum shells 1002*a*-1002*d* may be tangentially joined to the spherical portion 1004 so that the minimum path length L is not changed.

In FIGS. 10A-10B, only four conical frustum shells are attached to a spherical portion. However, it is noted that other suitable number of conical frustum shells may be tangentially joined to the spherical portion so that the minimum path length is not changed while the volume of the container is increased.

In some cases, the aperture angle, 2θ, of the light frustum 422*a* in FIG. 6 may be so large that the conical frustum shell 402*a* in FIG. 4 cannot be matched to the light cone 422*a*. In such a case, the light source modules may be mounted on other portion than the top portions of the conical frustum shells 402*a* and 402*b*. FIG. 11 shows a perspective view of a fluid disinfection apparatus 1100 according to embodiments of the present disclosure. FIG. 12 shows a light frustum from a light source module 1110 in FIG. 11 according to embodiments of the present disclosure. As depicted, the fluid disinfection apparatus 1100 may include: a container 1101; an inlet 1104*b*; an outlet 1104*a*; and one or more light source modules 1110 mounted to the container 1101. In embodiments, each light source module may include one or more ultraviolet light emitting diodes (UV LEDs). In embodiments, the container 1101 may include two conical frustum shells 1102*a* and 1102*b*, where the bases of the conical frustum shells 1102*a* and 1102*b* are joined to form a circular ring 1103, and the light source modules 1110 may be detachably mounted to the circular ring 1103 along the circumferential direction of the circular ring. In embodiments, the fluid disinfection apparatus 1100 may further include one or more monitor windows 1130*a* and 1130*b* that are similar to the monitor windows 430*a* and 430*b*, respectively.

In embodiments, the light frustum 1142 may have an aperture angle, 2θ, where the angle 1140 between the two conical frustum shells 1102a and 1102b at the circular ring 1103 may be substantially the same as the aperture angle, 2θ. The angle 1140 refers to the angle between the sides of the two conical frustum shells 1102a and 1102b measured on a plane that passes through both the apex and the center of the base of the conical frustum shell 1102a (or 1102b). In embodiments, the two conical frustum shells 1102a and 1102b have the same aperture angles, and in such as case, aperture angle 2α of the conical frustum shells may satisfy the Equation: 2α+2θ=180°, i.e., the aperture angles 2α and 2θ are supplementary angles.

FIG. 13A shows an exploded cross sectional view of the light source assembly 1300, taken along the line 13A-13A according to embodiments of the present disclosure. FIG. 13B shows a perspective view of the light source module 1110 according to embodiments of the present disclosure. As depicted, the light source assembly 1300 may include: a mount 1302 for mounting a light source module 1110 thereto; a window 1304 formed of a material transparent to the disinfection light; an O-ring 1306 disposed between the window 1304 and mount 1302; the light source module 1110; and a nut 1308 for detachably securing the light source module 1110 to the mount 1302. In embodiments, the mount 1302 may be a part of the circular ring 1103 and dimensioned to receive the light source module 1110.

In embodiments, the light source module 1110 may include: a housing 1322 having a thread 1323 form on the outer surface thereof; a heat sink 1328; a board 1326, such as PCB or copper board, mounted on the heat sink 1328; a light source 1324 mounted on the board 1326 and generating the disinfection light; and a cable 1330 coupled to the board 1326 and providing electrical power and signals for controlling the light source 1324.

In embodiments, the nut 1308 may engage the thread 1323 formed on the outer surface of the housing 1322 to detachably secure the light source module 1110 to the mount 1302. Upon turning the nut 1308, the window 1304 may push the O-ring 1306 against the mount 1302 so that the O-ring 1306 provides a sealing between the mount 1302 and the window 1304.

In embodiments, the heat sink 1328 may have a thread formed on its outer surface that engages a thread 1329 formed on the inner surface of the housing 1322. In embodiments, the heat energy generated by the light source 1324 may be transferred to the heat sink 1328 and subsequently, to the housing 1322 and the mount 1302. In embodiments, the heat sink 1328, housing 1322, and mount 1302 may be formed of materials, such as metals, having high thermal conductivities so that the heat energy is discharged into the water in the container 1101. Thus, in embodiments, unlike the disinfection device 300, the light source module 1110 may not include a cooling mechanism. Also, in embodiments, unlike the disinfection device 300, the light source module 1110 may not include a reflector for guiding the light from the light source 1324.

Figure 14:
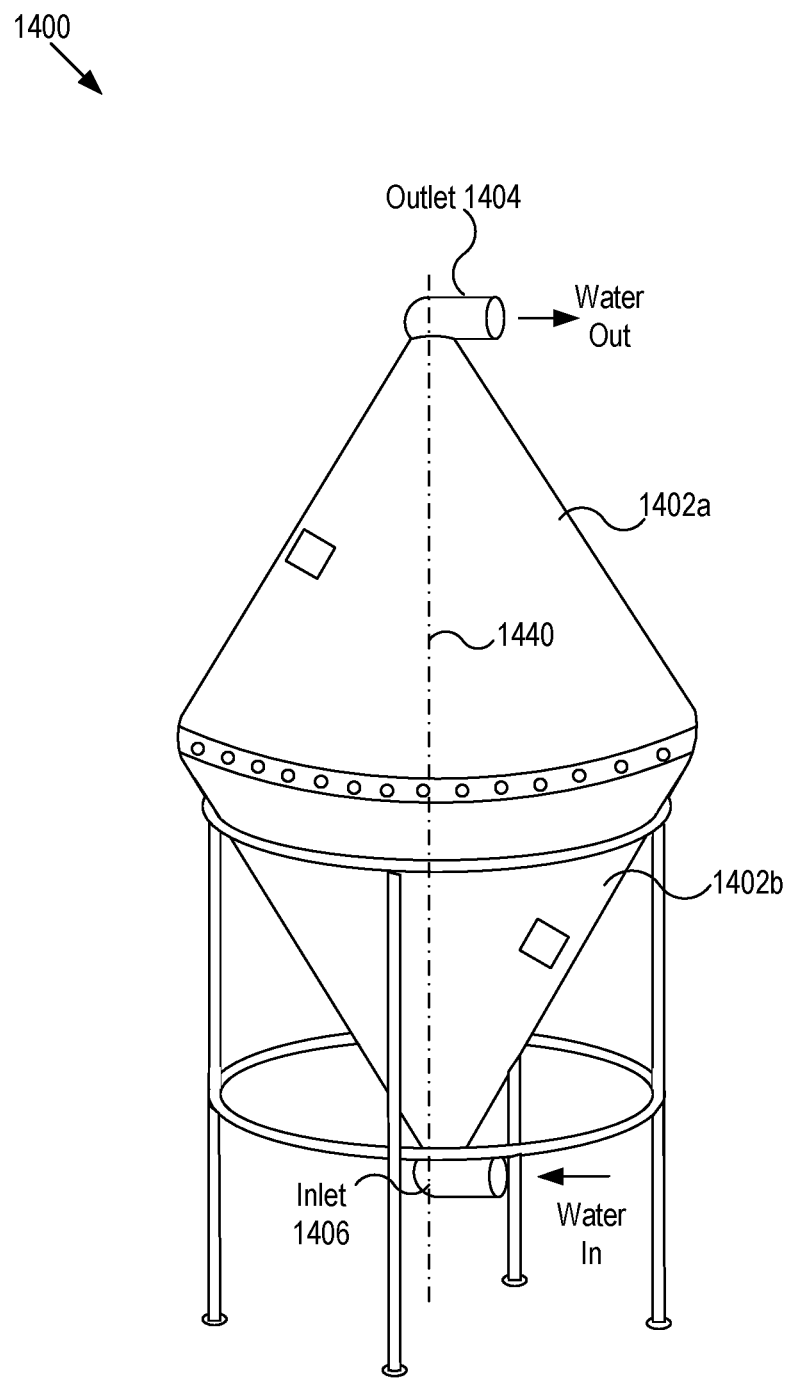
FIG. 14 shows a perspective view of a fluid disinfection apparatus according to embodiments of the present disclosure.

It is noted that the fluid disinfection apparatus in FIGS. 4-14 may have various modifications. For instance, FIG. 14 shows a perspective view of a fluid disinfection apparatus 1400 according to embodiments of the present disclosure. As depicted, the fluid disinfection apparatus 1400 may be similar to the fluid disinfection apparatus 1100 in FIG. 11, with the difference that the inlet 1406 and the outlet 1404 may be arranged in a direction normal to the vertical axis 1440, where the vertical axis 1440 passes through the apexes of the conical frustum shells 1402a and 1402b.

Figure 16:
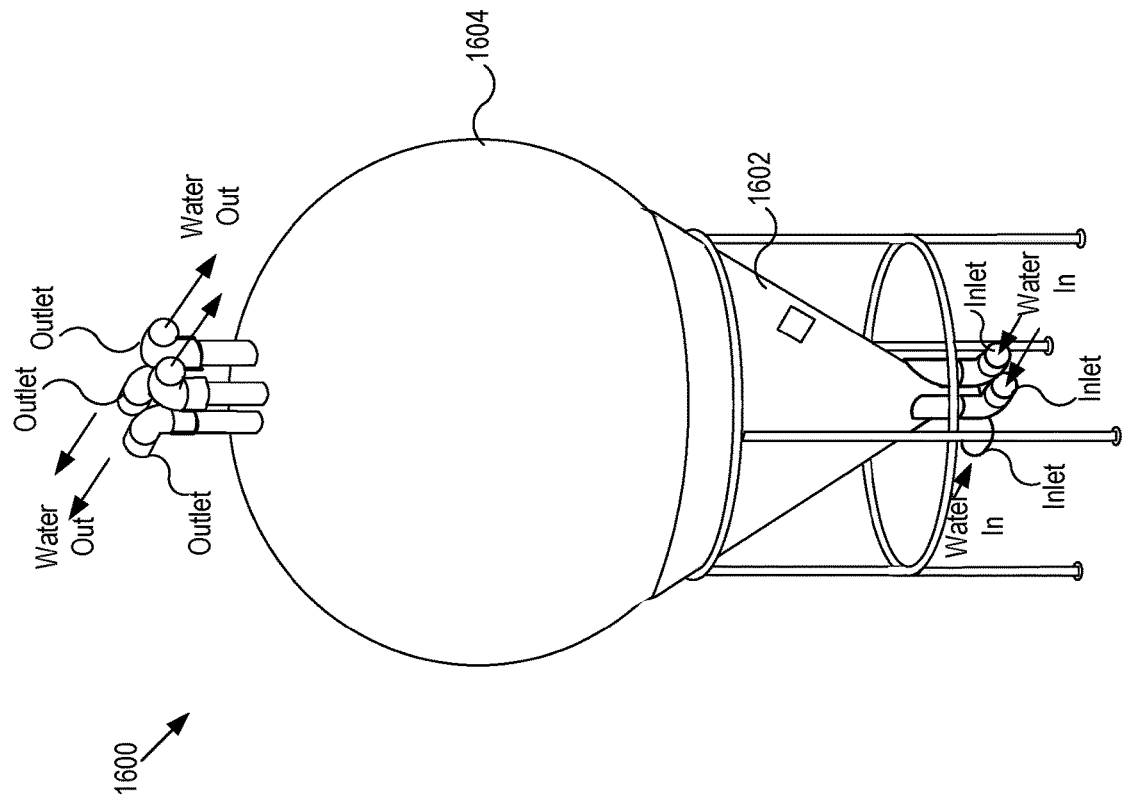
FIG. 16 shows a perspective view of a fluid disinfection apparatus according to embodiments of the present disclosure.
Figure 15:
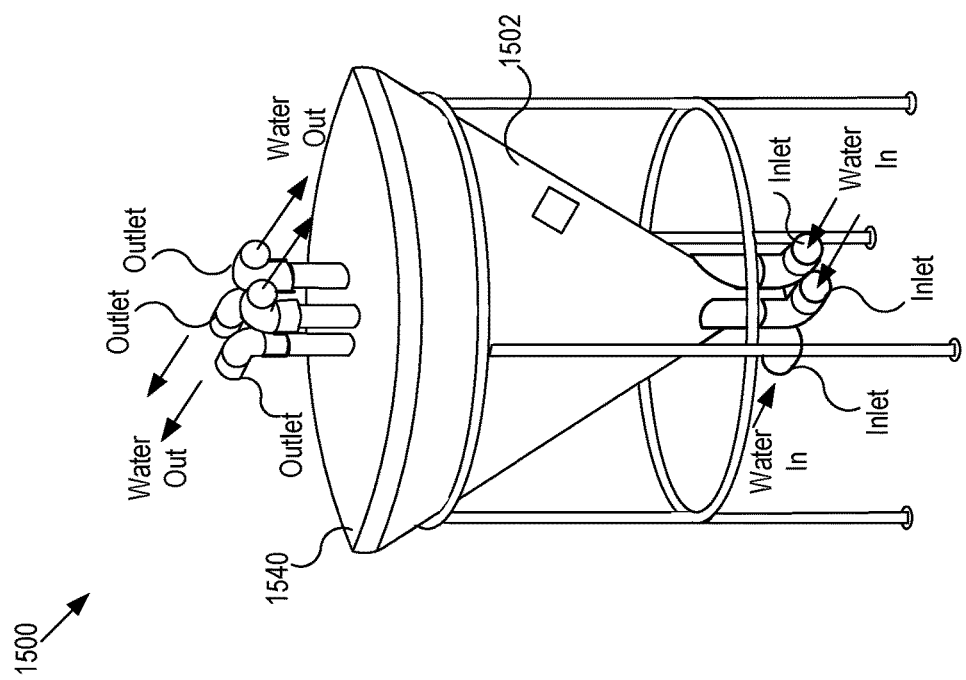
FIG. 15 shows a perspective view of a fluid disinfection apparatus according to embodiments of the present disclosure.

FIG. 15 shows a perspective view of a fluid disinfection apparatus 1500 according to embodiments of the present disclosure. As depicted, the fluid disinfection apparatus 1500 may be similar to the fluid disinfection apparatus 400 in FIG. 4, with the difference that the container has only one conical frustum shell 1502 that is joined to a cap 1540. FIG. 16 shows a perspective view of a fluid disinfection apparatus 1600 according to embodiments of the present disclosure. As depicted, the fluid disinfection apparatus 1600 may be similar to the fluid disinfection apparatus 900 in FIG. 9, with the difference that the container has only one conical frustum shell 1602, where the conical frustum shell 1602 is tangentially joined to a portion of a spherical shell 1604.

Figure 17B:
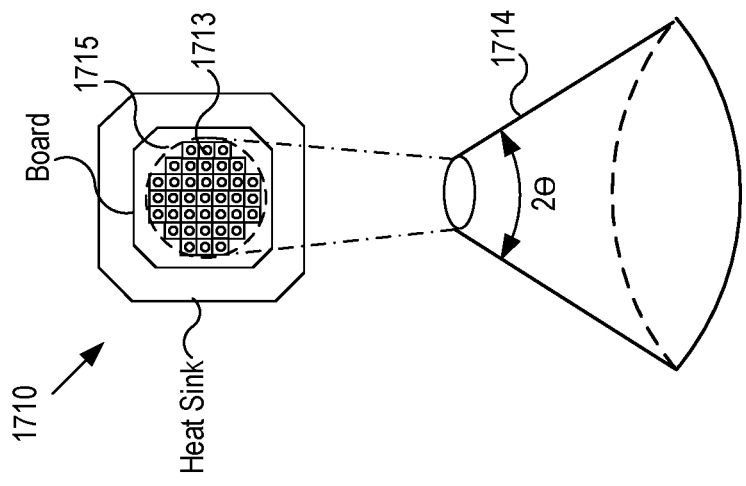
FIG. 17B shows a top view of a light source module and a perspective view of a disinfection light cone from the light source module according to embodiments of the present disclosure.
Figure 17A:
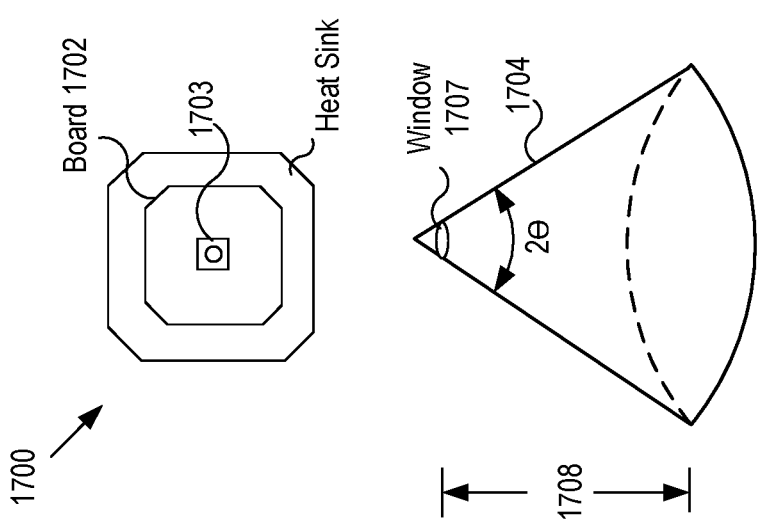
FIG. 17A shows a top view of a light source module and a perspective view of a disinfection light cone from the light source module according to embodiments of the present disclosure.

In embodiments, light emitted from LED light sources may diverge in space and may not be collimated. In embodiments, to maximize UV light disinfection efficiency, the volume of the fluid to be disinfected may be preferred to coincide with the light cone, pyramid or frustum delivered by the disinfection light source (UV LED or LED light panel). In embodiments, the disinfection light cone, pyramid, or frustum may be engineered by arrangements of UV LED arrays and reflectors. In embodiments, the disinfection light source, such as ultraviolet (UV) light-emitting diode (LED), may be a small light source emitting light within a certain solid angle and considered to be a point light source. Then, the light within the solid angle may form a light cone. FIG. 17A shows a top view of a light source module 1700 and a perspective view of a disinfection light cone 1704 from the light source module 1700 according to embodiments of the present disclosure. In embodiments, the light source module 1700 may be similar to the light source module 300 in FIG. 3A, with the difference that the light source module 1700 does not include a reflector. As depicted, the light source 1703 mounted on a board 1702 may be a small light source and, as such, considered to be a point light source, and the disinfection light cone 1704 may have an aperture angle 2θ. In embodiments, the light source 1703 may include only one UV LED or a plurality of LEDs having a small dimension. It is noted that the light from the light source module 1700 passes through a window 1707, which is similar to the window 446 (shown in FIG. 7). As such, in embodiments, only the frustum portion 1708 of the light from the light source module 1700 may be located within the container.

In embodiments, an array of UV LEDs may form a light emitting panel, able to deliver a light pyramid, or a light frustum, depending on the light panel area size and the reflector geometry used in connection with the light panel. FIG. 17B shows a top view of a light source module 1710 and a perspective view of a disinfection light frustum 1714 from the light source module 1710 according to embodiments of the present disclosure. In embodiments, the light source module 1710 may be similar to the light source module 1700, with the difference that the dimension of the light source 1713 may be so large that the light source 1713 may not be considered as a point light source. As depicted, the light source 1713 may include a plurality of LEDS that are arranged in a substantially circular array pattern 1715. In such a case, the light generated by the light source 1713 may have a shape of a frustum 1714.

Figure 17D:
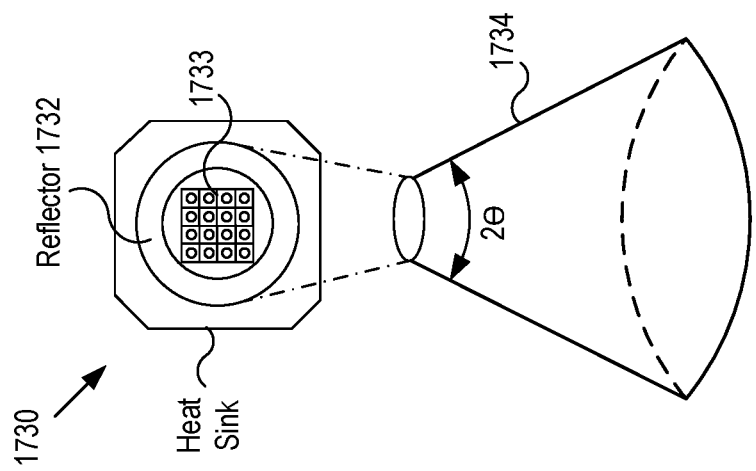
FIG. 17D shows a top view of a light source module and a perspective view of a disinfection light cone from the light source module according to embodiments of the present disclosure.
Figure 17C:
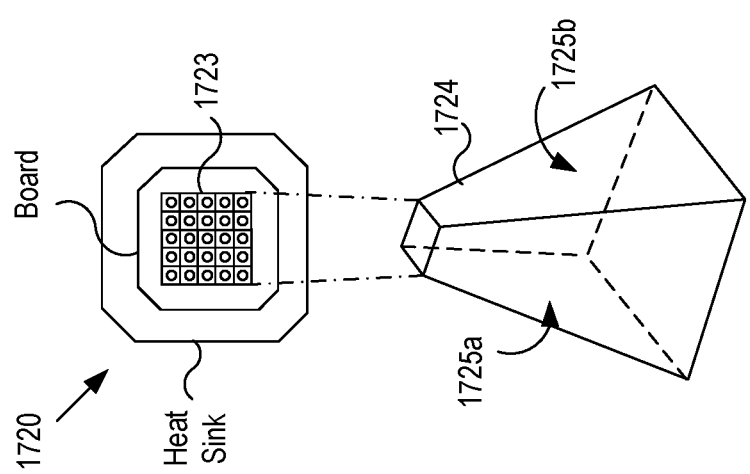
FIG. 17C shows a top view of a light source module and a perspective view of a disinfection light cone from the light source module according to embodiments of the present disclosure.

FIG. 17C shows a top view of a light source module 1720 and a perspective view of a disinfection light frustum of pyramid 1724 from the light source module 1720 according to embodiments of the present disclosure. In embodiments, the light source module 1720 may be similar to the light source module 1700, with the difference that the dimension of the light source 1723 may be so large that the light source 1723 may not be considered as a point light source. As depicted, the light source 1723 may include a plurality of LEDS that are arranged in a rectangular array pattern. In such a case, the light generated by the light source 1723 may have a shape of a frustum of a pyramid 1724. It should be apparent to those of ordinary skill in the art that the plurality of LEDS in the light source 1723 may be arranged so that the base of the disinfection light frustum of pyramid 1724 may have other suitable polygonal shape.

It is noted that the light source module 1720 may be installed on the circular ring 1103 (shown in FIG. 11). In such a case, the aperture angle of the light frustum 1724 may be defined as the angle between two opposite lateral sides 1725a and 1725b.

The light source modules in FIGS. 17A-17C may include a reflector, which is similar to the reflector 304, to change the shape of the light cone, frustum or pyramid. FIG. 17D shows a top view of a light source module 1730 and a perspective view of a disinfection light cone 1734 from the light source module 1730 according to embodiments of the present disclosure. As depicted, the light source module 1730 may be similar to the light source module 1720, with the difference that the light source module 1730 may include a reflector 1732. In embodiments, the light source 1733 may generate a light frustum of pyramid that is similar to the pyramid frustum 1724, while the reflector 1732 may change the light frustum of pyramid into the circular conical frustum 1734. Likewise, a reflector having a shape of a frustum of pyramid (not shown in FIG. 17D) may be included in the light source module 1710 so that the circular conical frustum 1714 may be changed into the frustum of pyramid 1724.

As discussed above, the light generated by the light source modules in FIGS. 17A-17D needs to pass through a window (such as 446), and as such, the light in the container may have a frustum shape. As such, hereinafter, the term light frustum collectively refers to the light that is generated by a light source module and located in a fluid container, where the base of the light frustum has a suitable geometry, such as triangle, circle, rectangle, polygon, etc.

Figure 18:
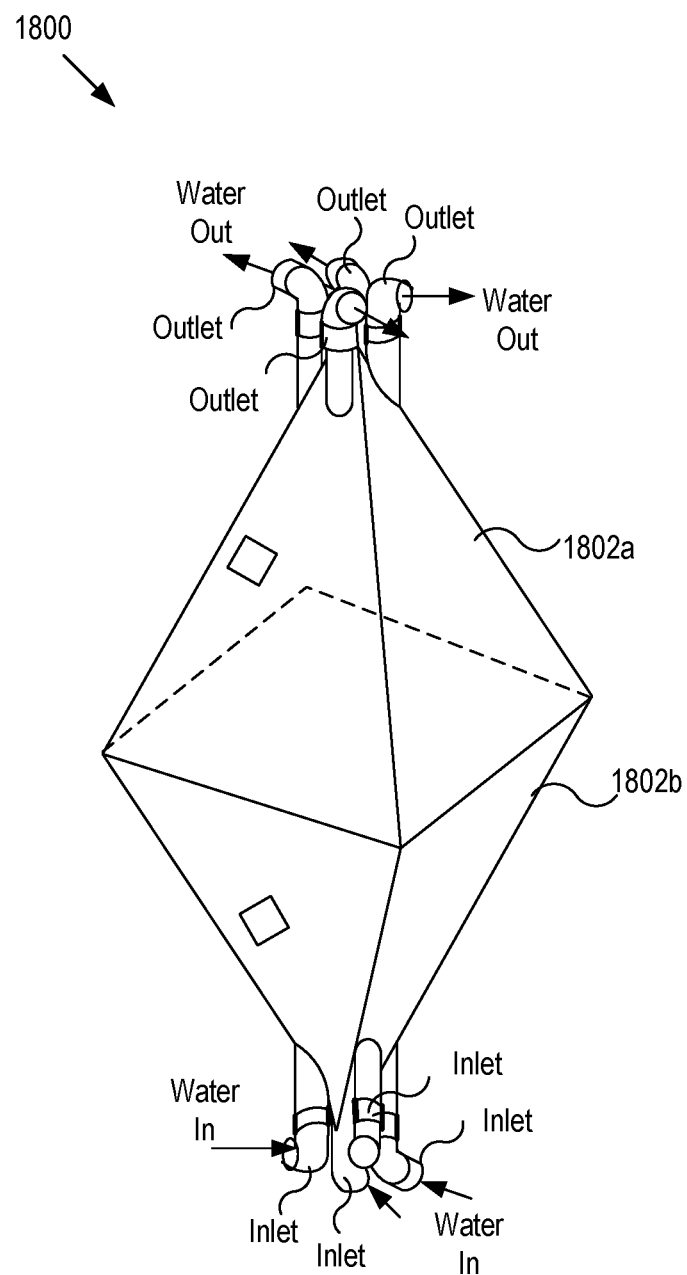
FIG. 18 shows a perspective view of a fluid disinfection apparatus according to embodiments of the present disclosure.

In FIGS. 3-10B and 14-17D, the bases of the light frusta have various geometrical shapes. In embodiments, a frustum shell of the container may have the same shape as the corresponding light frustum. FIG. 18 shows a perspective view of a fluid disinfection apparatus 1800 according to embodiments of the present disclosure. As depicted, the fluid disinfection apparatus 1800 may be similar to the fluid disinfection apparatus 400, with the difference that the container has two pyramid frustum shells 1802a and 1802b and that two light source modules (not shown in FIG. 18) that are similar to the light source module 1720 may be disposed respective top portions of the two pyramid frustum shells. In embodiments, the volume (space) of disinfection defined by the top, base and inner lateral surface of the pyramid frustum shell 1802a (or 1802b) may be located within the disinfection light frustum 1724.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A fluid disinfection apparatus, comprising:
   a first light source assembly for generating disinfection light that has a shape of a frustum; and
   a container for holding fluid therein, the container including:
   a first frustum shell defining a space surrounded by a top, a base, and an inner lateral surface thereof, the inner lateral surface of the first frustum shell being substantially identical to a lateral surface of the frustum of the disinfection light,
   wherein the first light source assembly is disposed over the top of the first frustum shell so that an entire portion of the space is substantially located within the frustum of the disinfection light; and
   a portion of a spherical shell,
   wherein a base of the first frustum shell is tangentially joined to the portion of the spherical shell.

2. The fluid disinfection apparatus of claim 1, further comprising:
   a second light source assembly for generating disinfection light that has a shape of a frustum,
   wherein the container further includes a second frustum shell and an inner lateral surface of the second frustum shell is substantially identical to a lateral surface of the frustum of the disinfection light generated by the second light source and wherein the second light source assembly is disposed under a top of the second frustum shell.

3. The fluid disinfection apparatus of claim 2,
   wherein a base of the second frustum shell is tangentially joined to the portion of the spherical shell.

4. The fluid disinfection apparatus of claim 2, further comprising:
   a plurality of inlets for introducing the fluid into the container, wherein the first light source assembly is disposed between the plurality of inlets; and
   a plurality of outlets for draining the fluid from the container, wherein the second light source assembly is disposed between the plurality of outlets.

5. The fluid disinfection apparatus of claim 1, further comprising:
   a window disposed on the first frustum shell and formed of a material that is transparent to the disinfection light.

6. The fluid disinfection apparatus of claim 5, further comprising:
   a sensor for measuring intensity of the disinfection light through the window.

7. The fluid disinfection apparatus of claim 1, wherein the first light source assembly comprises:
   a mount disposed on the first conical frustum shell;
   a window through which the disinfection light passes and detachably secured to the mount; and
   a light source module detachably secured to the mount and including:
   a light source for radiating the disinfection light;
   a board secured to the light source and configured to control the light source; and
   a heat sink for removing heat energy generated by the light source.

8. The fluid disinfection apparatus of claim 7, wherein the light source module further includes:
   a reflector for guiding the disinfection light into the shape of the frustum.

9. The fluid disinfection apparatus of claim 7, wherein the light source includes one or more ultraviolet light emitting diodes (UV LEDs).

10. The fluid disinfection apparatus of claim 9, wherein the UV LEDs are arranged in a circular array pattern.

11. The fluid disinfection apparatus of claim 9, wherein the UV LEDs are arranged in a rectangular array pattern.

12. The fluid disinfection apparatus of claim 1, wherein a base of the frustum of the disinfection light has a shape of triangle, circle, rectangle or polygon.

13. A fluid disinfection apparatus, comprising:
- a plurality of light source assemblies, each of the plurality of light source assemblies being configured to generate disinfection light that has a shape of a conical frustum; and
- a container for holding fluid therein, the container including:
  - a first conical frustum shell; and
  - a second conical frustum shell, a base of the first conical frustum shell being joined to a base of the second conical frustum shell to form a circular ring, the plurality of light source assemblies being disposed along a circumferential direction of the circular ring,
- wherein an aperture angle of the conical frustum of the disinfection light is substantially same as an angle between the first and second conical frustum shells at the circular ring.

14. The fluid disinfection apparatus of claim 13, further comprising:
- at least one inlet for introducing the fluid into the container and disposed on a top portion of first conical frustum shell; and
- at least one outlet for draining the fluid from the container and disposed on a top portion of second conical frustum shell.

15. The fluid disinfection apparatus of claim 13, wherein each of the plurality of light source assemblies comprises:
- a mount disposed on the circular ring;
- a window formed of a material that is transparent to the disinfection light and detachably mounted to the mount; and
- a light source module mounted to the mount and including:
  - a housing;
  - a light source for radiating the disinfection light and disposed in the housing; and
  - a heat sink detachably secured to the housing and configured to transfer heat energy from the light source to the housing.

16. The fluid disinfection apparatus of claim 15, wherein each of the plurality of light source assemblies further comprises;
- a nut for detachably mounting the light source module to the mount and configured to transfer the heat energy from the housing to the mount.

17. The fluid disinfection apparatus of claim 15, wherein the light source includes one or more ultraviolet light emitting diodes (UV LEDs).

* * * * *